United States Patent
Sayo et al.

[11] Patent Number: 4,764,629
[45] Date of Patent: Aug. 16, 1988

[54] RUTHENIUM-PHOSPHINE COMPLEX

[75] Inventors: Noboru Sayo, Kanagawa; Takanao Taketomi, Chiba; Hidenori Kumobayashi; Susumu Akutagawa, both of Kanagawa, all of Japan

[73] Assignee: Takasago International Corporation, Tokyo, Japan

[21] Appl. No.: 125,280

[22] Filed: Nov. 25, 1987

[30] Foreign Application Priority Data

Nov. 27, 1986 [JP] Japan .................. 61-282968

[51] Int. Cl.$^4$ ............................................ C07F 15/00
[52] U.S. Cl. ........................................ 556/23; 546/2; 546/11
[58] Field of Search ................... 556/23; 546/2, 11

[56] References Cited

U.S. PATENT DOCUMENTS 4,604,474 8/1986 Kumobayashi et al. .......... 556/23 X
4,605,750 8/1986 Kumobayashi et al. .......... 556/23 X
4,691,037 9/1987 Yushikawa et al. ............... 556/23 X Primary Examiner—Paul F. Shaver
Attorney, Agent, or Firm—Sughrue, Mion, Zinn, Macpeak & Seas

[57] ABSTRACT

A ruthenium-phosphine complex represented by formula (I):

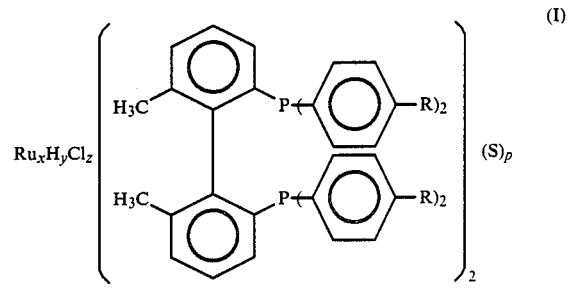

wherein R represents a hydrogen atom, a methyl group, or a methoxy group; S represents a tertiary amine; when y is 0, then x is 2, z is 4, and p is 1; and when y is 1, then x is 1, z is 1, and p is 0. The complex is inexpensive and exhibits excellent performance as a catalyst for various organic syntheses, and particularly asymmetric hydrogenation.

3 Claims, No Drawings

RUTHENIUM-PHOSPHINE COMPLEX

FIELD OF THE INVENTION

This invention relates to a ruthenium-phosphine complex useful as a catalyst for various organic syntheses and asymmetric syntheses, such as asymmetric hydrogenation and asymmetric isomerization.

BACKGROUND OF THE INVENTION

Various organic synthetic reactions using metal complexes have hitherto been developed and utilized for many purposes. In particular, there are a number of reports on asymmetric catalysts to be used in asymmetric syntheses, i.e., asymmetric isomerization, asymmetric hydrogenation, and the like. Of the reported asymmetric catalysts, metal complexes formed between metallic rhodium and an optically active tertiary phosphine are especially well known as catalysts for asymmetric hydrogenation. Such complexes typically include a rhodium-phosphine complex using 2,2'-bis(diphenylphosphino)-1,1'-binaphthyl (hereinafter abbreviated as BINAP) as a ligand as disclosed in Japanese Patent Application (OPI) No. 61937/80 (the term "OPI" as used herein means an "unexamined published Japanese patent application") and a rhodium-phosphine complex using 2,2'-bis(diphenylphosphino)-6,6'-dimethylbiphenyl as a ligand as disclosed in Japanese Patent Application (OPI) No. 65051/84.

On the other hand, known ruthenium complexes, though there are not so many reports as compared with rhodium complexes, include those having BINAP or 2,2'-bis(di-p-tolylphosphino)-1,1'-binaphthyl (hereinafter abbreviated as T-BINAP) as a ligand, e.g., $Ru_2Cl_4$(BINAP)$_2$-(NEt$_3$) (wherein Et represents an ethyl group, hereinafter the same), $Ru_2Cl_4$(T-BINAP)$_2$-(NEt$_3$), RuHCl(BINAP)$_2$, and RuHCl(T-BINAP)$_2$, as reported in Ikariya et al., *J. Chem. Soc., Chem. Commun.*, p. 922, (1985). However, the stateof-the-art ruthenium complexes are not satisfactory in stability as well as optical yield attained.

Although metallic rhodium provides excellent complex catalysts, it is expensive due to limitations in place and quantity of production. When used as a catalyst component, it forms a large proportion in cost of the catalyst, ultimately resulting in increase in cost of the final commercial products. While metallic ruthenium is cheaper than rhodium and appears promising as a catalyst component for industrial application, it still has problems in its activity to cope with precision reactions and its range of application. Therefore, it has been keenly demanded to develop a catalyst which is inexpensive, has high activity and durability, and catalyzes asymmetric reactions to attain high optical yields, i.e., to produce reaction products having high optical purity.

SUMMARY OF THE INVENTION

As a result of extensive investigations with the purpose of meeting the above-described industrial demand, the inventors have discovered a novel ruthenium complex having high catalytic activity, which is usable either for general syntheses when the ligand thereof is optically inactive or for asymmetric syntheses when the ligand thereof is optically active. The present invention has been completed based on this finding.

The present invention relates to a ruthenium-phosphine complex represented by formula (I)

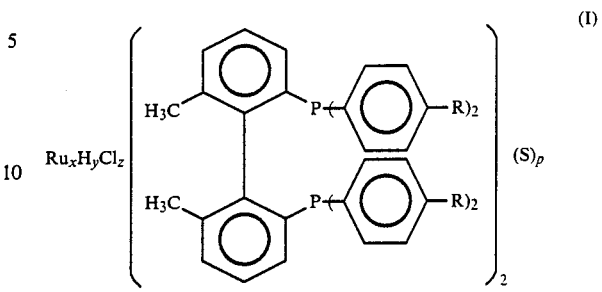

wherein R represents a hydrogen atom, a methyl group, or a methoxy group; S represents a tertiary amine; when y is 0, then x is 2, z is 4, and p is 1; and when y is 1, then x is 1, z is 1, and p is 0.

DETAILED DESCRIPTION OF THE INVENTION

The novel ruthenium-phosphine complex of formula (I) according to the present invention can be prepared easily by reacting [RuCl$_2$(COD)]$_n$ (wherein COD represents cyclooctadiene, hereinafter the same) and a 2,2'-bis(diarylphosphino)-6,6'-dimethylbiphenyl in a solvent in the presence of a tertiary amine.

The above reaction produces two kinds of compounds depending on selections of the molar ratio of the starting materials and the kind of the solvent used. More specifically, the compounds of formula (I) wherein y is 0, x is 2, z is 4, and p is 1 can be obtained in good yield by reacting 1 mole of [RuCl$_2$(COD)]$_n$ with about 1.2 moles of a 2,2'-bis(diarylphosphino)-6,6'-dimethylbiphenyl and about 4 moles of a tertiary amine, e.g., triethylamine, tributylamine, N-methylpiperidine, ethyldiisopropylamine, etc., in a solvent, e.g., benzene, toluene, xylene, etc., under heating. The ruthenium-phosphine complexes of formula (I) wherein y is 1, x is 1, z is 1, and p is 0 can be obtained in good yield by reacting 1 mole of [RuCl$_2$(COD)]$_n$ with about 2 moles of a 2,2'-bis(diarylphosphino)-6,6'-dimethylbiphenyl and about 4 moles of the above-recited tertiary amine in a solvent having reducing properties, e.g., methanol, ethanol, etc., under heating.

The starting material, [RuCl$_2$(COD)]$_n$, can be prepared by reacting ruthenium chloride and cycloocta-1,5-diene in an ethanol solvent as taught in M.A. Bennett et al., *Chemistry and Ind.*, p. 1516 (1959).

The 2,2'-bis(diarylphosphino)-6,6'-dimethylbiphenyl, the other starting material, can be synthesized according to the process reported in Miyashita et al., *The Chemical Society of Japan, Collected Drafts II for Lectures in the* 52th *Spring Annual Meeting*, IT06, p. 1267 (1986). More specifically, o-toluidine is reacted with nitric acid to form 2-amino-3-methylnitrobezene, which is then converted to 2-iodo-3-methylnitrobenzene making use of the process described in P.B. Carlin et al., *J. Am. Chem. Soc.*, Vol. 78, p. 1997 (1956). A copper powder is reacted on the resulting product to obtain 2,2'-dinitro-6,6'-dimethylbiphenyl, which is then subjected to hyrogenation using a Raney nickel as a catalyst to obtain 2,2'-diamino-6,6'-dimethylbiphenyl. The product is treated with a 47% hydrobromic acid aqueous solution to obtain 2,2'-dibromo-6,6'-dimethylbiphenyl. A Grignard reagent is prepared from the product according to a process generally employed therefor, for example, by using magnesium. The resulting Grignard reagent is condensed with a diarylphosphinyl chloride selected from diphenylphosphinyl chloride, di-p-tolylphosphinyl chloride, and di-p-anisylphosphinyl chloride to obtain a (±)-2,2'-bis(diarylphosphino)-6,6'-dimethylbiphenyl. The product is resolved by using benzoyl tartrate and then reduced with trichlorosilane to obtain an optically active 2,2'-bis(diarylphosphino)-6,6'-dimethylbiphenyl. Starting with the thus prepared optically active 2,2'-bis(diarylphosphino)-6,6'-dimethylbiphenyl, there can be obtained the ruthenium-phosphine complex of the present invention having the corresponding optical activity.

Specific examples of the ruthenium-phosphine complex according to the present invention are shown below. In the following structural formulae, Bu represents an n-butyl group; and iPr represents an isopropyl group.

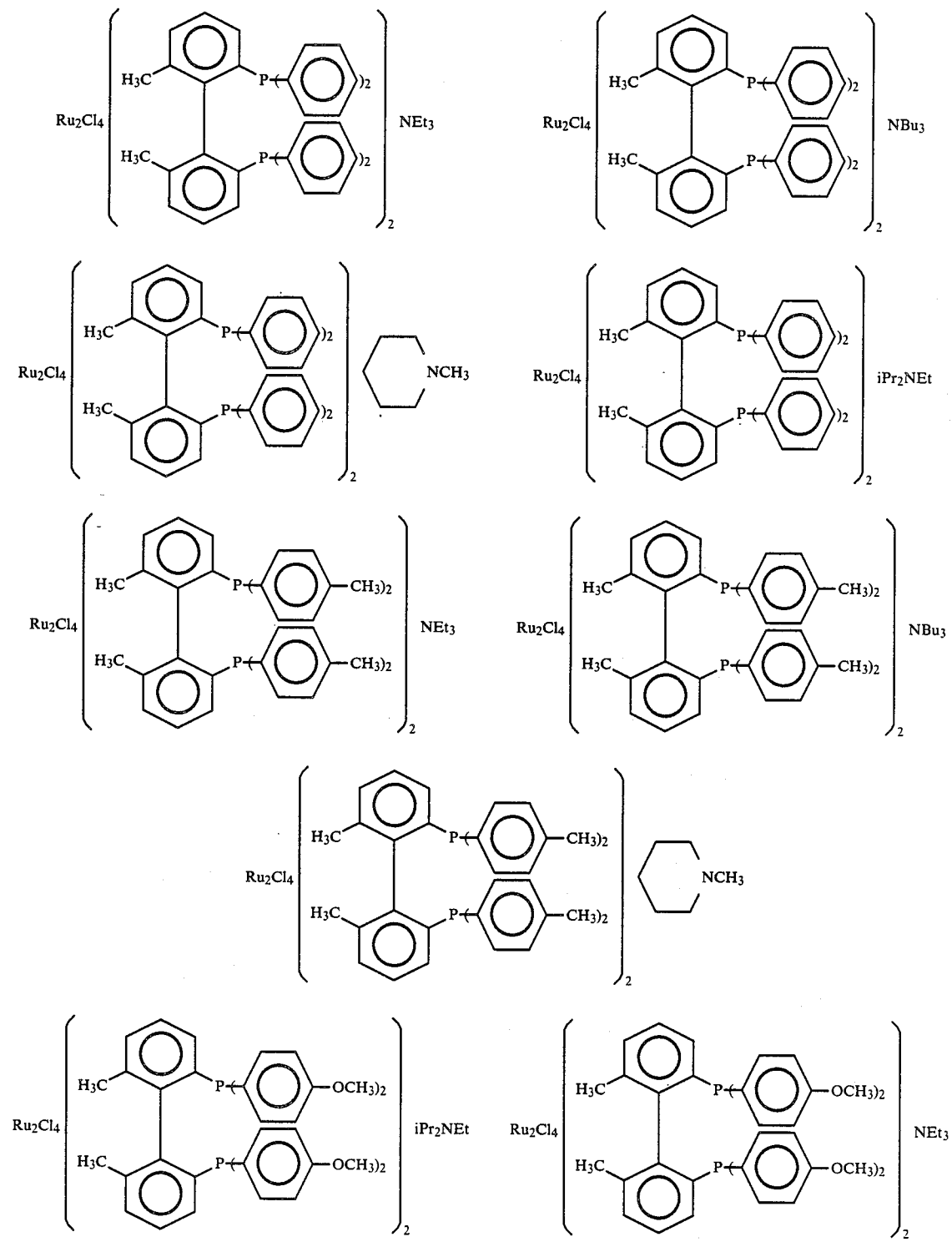

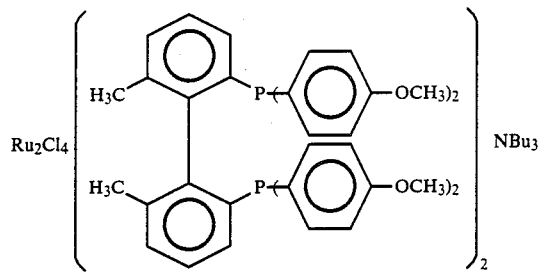

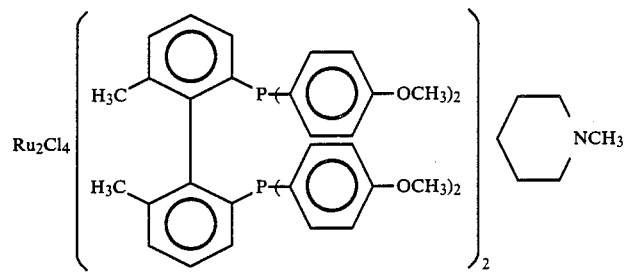

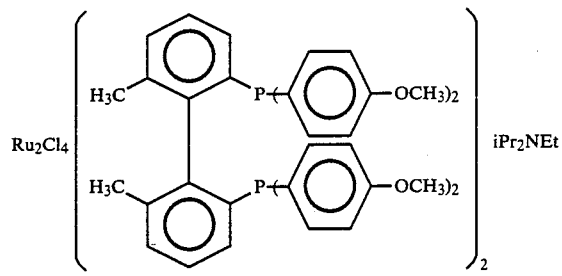

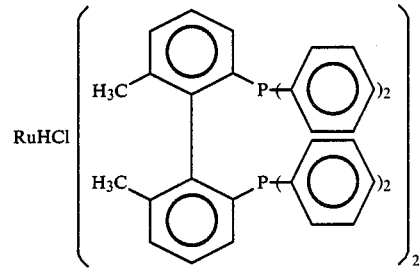

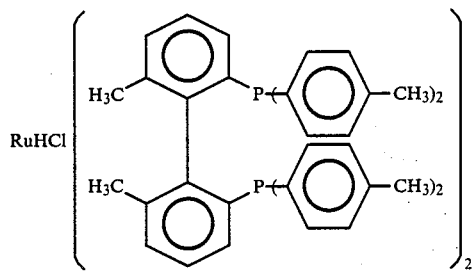

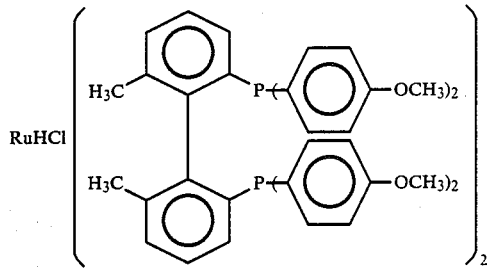

The ruthenium-phosphine complex of formula (I) according to the present invention contains a biphenyl basic structure as a ligand that exhibits higher structural flexibility and higher solubilities to various solvents and is, therefore, more applicable to various reactions as compared with a BINAP ligand. For example, when the ruthenium-phosphine complex of the invention is applied to asymmetric hydrogenation reaction of dehydroamino acids, such as α-benzamidocinnamic acid, the reaction proceeds smoothly at a temperature of from 30° to 35° C. to produce an amino acid derivative, i.e., a hydrogenation product, at a selectivity reaching nearly 100%. Further, the thus produced amino acid has an optical purity of from 89 to 95%. Thus, the rutheniumphosphine complexes according to the present invention show very excellent activities as industrially useful catalysts.

The present invention will hereinafter be illustrated in greater detail with reference to Examples and Use Examples, but it should be understood that the present invention is not deemed to be limited thereto.

EXAMPLE 1

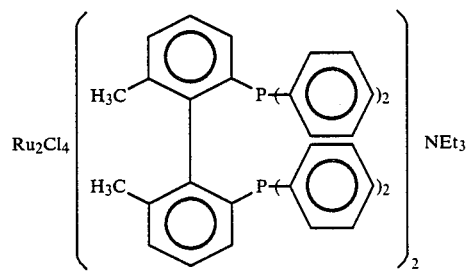

[Bis(μ,μ'-dichloro)bis{2,2'-bis(diphenylphosphino)-6,6'-dimethylbiphenyl}]diruthenium-Triethylamine To 50 ml of toluene were added 0.5 g (1.8 mmoles) of [RuCl$_2$(COD)]$_n$, 1 g (1.82 mmoles) of 2,2'-bis(diphenylphosphino)-6,6'-dimethylbiphenyl, and 1.0 ml (7.2 mmoles) of triethylamine under a nitrogen atmosphere, and the mixture was stirred while heating under toluene refluxing for 6 hours to effect reaction. The solvent was removed from the reaction mixture by distillation, and the residue was dried under reduced pressure. The solid was dissolved in methylene chloride, followed by filtration through Celite. The filtrate was concentrated to dryness under reduced pressure to obtain 1.35 g of the titled compound as deep red crystals. The yield was 97%.

Elemental Analysis for C$_{82}$H$_{79}$P$_4$NCl$_4$Ru$_2$: Calcd. (%): Ru 13.07, P 8.01, C 63.69, H 5.15. Found (%): Ru 12.71, P 7.64, C 64.07, H 5.52.

$^{31}$P NMR (CDCl$_3$) δppm: 51.63 (d, J=40.0 Hz), 52.52 (d, J=41.5 Hz).

$^1$H NMR (CDCl$_3$) δppm: 1.27 (s, 12H), 1.30 (br. s, 9H), 2.91–3.08 (m, 6H), 6.58–8.18 (m, 52H).

EXAMPLE 2

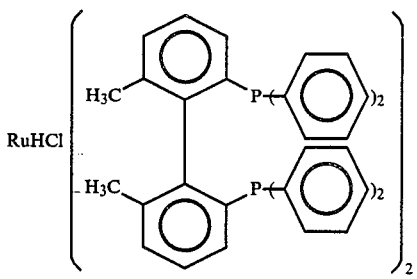

Chlorohydridobis[2,2'-bis(diphenylphosphino)-6,6'-dimethylbiphenyl]ruthenium

To 10 ml of ethanol were added 0.1 g (0.36 mmole) of [RuCl$_2$(COD)]$_n$, 0.47 g (0.86 mmole) of 2,2'-bis(diphenylphosphino)-6,6'-dimethylbiphenyl, and 0.2 mol (1.44 mmoles) of triethylamine under a nitrogen atmosphere, followed by heating under ethanol refluxing with stirring for 6 hours. The solvent was removed by distillation, and the residue was dried under reduced pressure. The solid was dissolved in methylene chloride, followed by filtration through Celite. The filtrate was concentrated to dryness under reduced pressure to obtain 0.43 g of the titled compound as a red solid. The yield was 96.4%.

Elemental Analysis for C$_{76}$H$_{65}$ClP$_4$Ru: Calcd. (%): Ru 8.16, P 10.00, C 73.69, H 5.29, Found (%): Ru 7.76, P 9.81, C 74.07, H 5.59.

$^{31}$P NMR (CDCl$_3$) δppm: 21.98 (t, J=35.2 Hz), 36.89 (t, J=35.2 Hz).

$^1$H NMR (CDCl$_3$) δppm: −16.50 (m, 1H), 1.35 (s, 12H), 6.58–7.73 (m, 26H).

USE EXAMPLE 1

In a 300 ml-volume autoclave were charged 7.6 mg (0.1 mmole) of the [bis(μ,μ'-dichloro)bis{2,2'-bis(diphenylphosphino)-6,6'-dimethylbiphenyl}]diruthenium-triethylamine as prepared in Example 1 and 1 g (4.87 mmoles) of acetylamidocinnamic acid, 50 ml of ethanol was added thereto. The mixture was allowed to react at 30° C. under a hydrogen pressure of 4 kg/cm$^2$ for 48 hours to produce N-acetylphenylalanine in a yield of 91%.

Optical Rotation, [α]$_D^{23}$ = −37.47° (c=3.26, methanol).

Optical Purity: 89.0%.

The present invention provides a novel ruthenium-phosphine complex exhibiting excellent performance as a catalyst for various organic syntheses, and particularly asymmetric hydrogenation, and shows industrially superior results in selective hydrogenation of olefins as well as in catalytic activity. Further, the complex according to the present invention can be produced at low cost, making a contribution to reduction of product price and, thus, has a high industrial value.

While the invention has been described in detail and with reference to specific embodiments thereof, it will be apparent to one skilled in the art that various changes and modifications can be made therein without departing from the spirit and scope thereof.

What is claimed is:

1. A ruthenium-phosphine complex represented by formula (I):

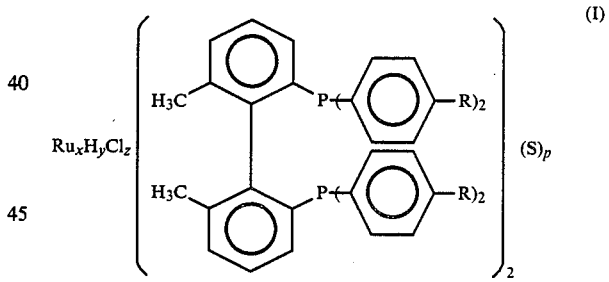

wherein R represents a hydrogen atom, a methyl group, or a methoxy group; S represents a tertiary amine; when y is 0, then x is 2, z is 4, and p is 1; and when y is 1, then x is 1, z is 1, and p is 0.

2. [Bis(μ,μ'-dichloro)bis{2,2'-bis(diphenylphosphino)-6,6'-dimethylbiphenyl}]diruthenium-triethylamine, according to claim 1.

3. chlorohydridobis[2,2'-bis(diphenylphosphino)-6,6'-dimethylbiphenyl]ruthenium, according to claim 1.

* * * * *